United States Patent [19]

Baker

[11] Patent Number: 5,643,780
[45] Date of Patent: Jul. 1, 1997

[54] COMPOSITIONS AND METHODS FOR MODULATING RNA ACTIVITY THROUGH MODIFICATION OF THE 5' CAP STRUCTURE OF RNA

[75] Inventor: Brenda F. Baker, Carlsbad, Calif.

[73] Assignee: ISIS Pharmaceuticals, Inc., Carlsbad, Calif.

[21] Appl. No.: 327,363

[22] Filed: Oct. 21, 1994

Related U.S. Application Data

[63] Continuation-in-part of Ser. No. 847,054, Apr. 3, 1992, abandoned.

[51] Int. Cl.⁶ .......................... C12N 5/10; C07H 21/00; C08B 37/00; A01N 59/16
[52] U.S. Cl. ................. 435/375; 536/24.5; 536/18.7; 514/44; 435/6; 435/325; 424/604; 424/617
[58] Field of Search ..................... 514/44; 536/24.5, 536/18.7; 935/33, 34, 35, 37, 38, 44, 46, 8, 76; 435/6, 240.1; 424/604, 617

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 4,999,421 | 3/1991 | Brunck et al. | 430/350 |
| 5,004,810 | 4/1991 | Draper | 536/27 |
| 5,034,506 | 7/1991 | Summerton | 528/391 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,166,195 | 11/1992 | Ecker | 514/44 |
| 5,194,428 | 3/1993 | Agrawal et al. | 514/44 |
| 5,242,906 | 9/1993 | Pagano et al. | 514/44 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |

FOREIGN PATENT DOCUMENTS

| | | | |
|---|---|---|---|
| WO8707300 | 12/1987 | WIPO. | |
| WO91/10671 | 7/1991 | WIPO. | |
| 9110671 | 7/1991 | WIPO | C07H 1/00 |

OTHER PUBLICATIONS

Miller and Ts'O "A New Approach to Chemotherapy Based on Molecular Biology and Nucleic Acid Chemistry: Matagen (Masking Tape for Gene Expression" *Anti-Cancer Drug Design* 2: 117–128, 1987.

Coppola, J. A., Field, A.S., and Luse, D.S. "Promoter-proximal Pausing by RNA Polymerase II in vitro: Transcripts Shorter than 20 Nucleotides are not Capped," (1983) *Proc. Natl. Acad. Sci.* 80:1251–1255.

Konarska et al., "Recognition of Cap Structure in Splicing In Vitro of mRNA Precursors," *Cell* 38:731–736, 1984.

Ross, Jeffrey, "Messenger RNA Turnover in Eukaryotic Cells," *Mol. Biol. Med.* 5: 1–14, 1988.

Green et al., "Human β-Globin Pre-mRNA Synthesized In Vitro Is Accurately Spliced in Xenopus Oocyte Nuclei," *Cell* 32: 681–694, 1983.

Hamm, J. and Mattaj, I.W. "Monomethylated Cap Structures Facilitate RNA Export from the Nucleus," *Cell* 63:109, 1990.

Shatkin, A.J., "Capping of Eucaryotic mRNAs," *Cell* 9: 645–653, 1976.

Filipowicz, Witold, "Functions of the 5'-Terminal mRNA," *Federation of Experimental Biologists Society Letter* 96: 1–11, 1978.

Sonenberg, "Cap–Binding Proteins of Eukaryotic Messenger RNA: Functions in Initiation and Control of Translation" *Prog. Nuc. Acid Res & Molec. Biol.* 35 173–207 (1988).

Shatkin, Aaron J., "mRNA Cap Binding Proteins: Essential Factors for Initiating Translation," *Cell* 40:223–224, 1985.

Nielsen, P.E., et al, "Sequence–Selective Recognition of DNA by Strand Displacment with a Thymine–Substituted Polyamide," *Science* 254:1497, 1991.

Sawadogo and Roeder, "Factors Involved in Specific Transcription by Human RNA Polymerase II: Analysis by a Rapid and Quantitative in vitro Assay," *Proc. Natl. Acad. Sci.* 82:4394–4398, 1985.

Degitz, K., et al., "Cloning and Characterization of the 5'-Transcriptional Regulatory Region of the Human Intercellular Adhesion Molecule 1 Gene," *J. Biol. Chem.* 266:14024–14030, 1991.

Sugiura, Y. and Hirayama, Y., "Structural and Electronic Effects on Complex Formation of Copper (II) and Nickel (II) with Sulfhydryl–containing Peptides" *Inorg. Chem.* 15:679–682 (1976).

Sugiura, Y., et al., "Copper (II) Complex of Sulfur–Containing Peptides. Characterization to the Chromophore in Blue Copper Proteins," *J. Am. Chem. Soc.* 97:5577–5581, 1975.

Sugiura, Y., "Newly Synthesized Sulfhydryl– and Imidazole–Containing Tripeptides with a Specific Copper–Binding Site" *Inorg. Chem.* 17:2176–2181 (1978).

Uhlmann, E. and A. Peyman, "Antisense Oligonucleotides: A New Therapeutic Principle," *Chem. Rev.* 90:543–584 (1990).

Stenberg, R.M., et al., "Multiple Spliced and Unspliced Transcripts from Human Cytomegalovirus Immediate–Early Region 2 and Evidence for a Common Initiation Site Within Immediate–Early Region 1," *J. Virol.* 56:665–675, 1985.

Stenberg, R.M., et al., "Structural Analysis of the Major Immediate Early Gene of Human Cytomegalovirus," *J. Virol.* 49:190–199, 1984.

(List continued on next page.)

*Primary Examiner*—Charles C. P. Rories
*Attorney, Agent, or Firm*—Woodcock Washburn Kurtz Mackiewicz & Norris

[57] ABSTRACT

Methods for regulating gene expression in biological experimental systems via modification or removal of the 5' cap structure of targeted ribonucleic acids are disclosed. Modification or removal of the 5' cap structure is achieved in accordance with preferred embodiments utilizing antisense compounds which are complementary to the 5' terminus of the targeted RNA and have attached to them reactive moieties explicitly designed for chemical modification or cleavage of the 5' cap structure of RNA. Compositions that have utility as research reagents and therapeutics for the treatment of diseases are disclosed.

27 Claims, 5 Drawing Sheets

OTHER PUBLICATIONS

Cory, S. and Adams, J.M., "The Modified 5'-Terminal Sequences in Messenger RNA of Mouse Myeloma Cells," *J. Mol. Biol.* 99: 519–547, 1975.

Dignam et al., "Accurate Transcription Initiation by RNA Polymerase II in a Soluble Extract from Isolated Mammalian Nuclei," *Nucl. Acids. Res.* 11:1475, 1983.

Toulme et al., "Antmessenger Oligodeoxyribonucleotides: An Alternative to Antisense RNA for Artificial Regulation of Gene Expression—A Review" *Gene* 72 (1–2): 51–58 (1988).

Rothenberg et al., "Oligodexoynucleotides as Anti–Sense Inhibitors of Gene Expression: Therapeutic Implications" J. of the Natl. Cancer Institute 81(20): 1539–1545 (1989).

Sambrook et al., "Molecular Cloning". A Laboratory Manual, 2nd Edition, Cold Spring Harbor Laboratory Press, vol. 2 p. 8.6 (1989).

Schultz, "The Interplay Between Chemistry and Biology in the Design of Enzymatic Catalysts" *Science* 240: 426–433 (1988).

Goodchild et al., "Inhibition of Human Immunodeficiency Virus Replication by Antisense Oligodeoxynucleotides" Proc. Natl. Acad. Sci. USA 85: 5507–5511 (1988).

Goodchild, J., Bioconjigate Chemistry, vol. 1 (3) ('90) pp. 165–187.

Goodchild, J., et al., Arch. Biochem. Biophys., vol. 263(2) ('88) 401–9.

Jamer, W., Antiviral Chem. & Chemotherapy ('90) vol. 2 (4) pp. 191–214.

Milligan, J., et al., J. Med. Chem., vol 36 (14) (9 Jul. '93) pp. 1923–1937.

Szein, C., et al., Science, vol. 261 (Aug. 20, 1993) pp. 1004–1012.

Tseng, B., et al., Cancer Gene Therapy, vol. 1 (1) (Mar. 1994) pp. 65–71.

Uhlmann, E., et al., Chem. Rev., vol. 90 (4) (Jun. 1990) pp. 543–584.

P. Wesbermann et al., Biomed, Biochim. Ana, vol. 48 (1) ('89) 85–93.

P. Verspiereu et al., Gene, vol. 61 (87) 307–15.

C. Szein et al., Cancer Res. 48 (May 13, 1988) 2659–68.

Sigman, "Nuclease Activity of 1,10-Phenanthroline-Copper Ion" *Acc. Chem. Res* 19:180–86 (1986).

Miller et al., "Nonionic Nucleic Acid Analogues. Synthesis and Characterization of Dideoxyribonucleoside Methylphosphonates" *Biochemistry* 18: 5134–5143 (1979).

Constant et al., "Heterodimeric Molecules Including Nucleic Acid Bases and 9-Aminoacridine Spectroscopic Studies, Conformations, and Interactions with DNA" *Biochemistry* 27:3997–4003 (1988).

Jager et al, "Oligonucleotide N-Alkylphosphoramidates: Synthesis and Binding to Polynucleotides" *Biochemistry* 27:7237–7246 (1988).

Stein and Cohen, "Oligodeoxynucleotides as Inhibitors of Gene Expression: A Review" *Cancer Res.* 48: 2659–68 (1988).

Rutherford and Morgan, "The Specific Chemical Cleavage of Pyrophosphate Diesters" *Can. J. Biochem.* 50: 287–291 (1972).

Brill et al, "Synthesis of Oligodeoxynucleoside Phosphorodithioates via Thioamidites" *Journal of the American Chemical Society* 111:2321–22 (1989).

Agarwal et al., "Synthesis and Enzymatic Properties of Deoxyribooligonucleotides Containing Methyl and Phenylphosphonate Linkages" *Nucleic Acid Research* 6:3009–24 (1979).

Letsinger et al., "Effects of Pendant Groups at Phosphorus on Binding Properties of d-ApA Analogues" *Nucleic Acid Research* 14: 3487–3499 (1986).

Cazenave et al., "Enzymatic Amplification of Translation Inhibition of Rabbi β-globin mRNA Mediated by Antimessenger Oligodeoxynucleotides Covalently Linked to Intercalating Agents" *Nucleic Acid Research* 15:4717–36 (1987).

Le Doan et al., "Sequence-Targeted Chemical Modifications of Nucleic Acids by Complementary Oligonucleotides Covalently Linked to Porphyrins" *Nucleic Acid Research* 15: 8643–59 (1987).

Darzynkiewicz et al., "β-globin mRNAs capped with $m^7G$, $m^{2,7_2}G$ or $m^{2,2,7_3}G$ differ in intrinsic translation efficiency" Nucleic Acid Research 16:8953 (1988).

Zon, Oligonucleotide Analogues as Potential Chemitherapeutic Agents" *Pharmaceutical Res.* 5:539–49 (1988).

Agrawal et al., "Oligodeoxynucleoside Phosphoramidates and Phosphorothioates as Inhibitors of Human Immunodeficiency Virus" *Proc. of the Natl. Acad of Science* 85:7079–7083 (1987).

Westheimer, "Why Nature Chose Phosphates" *Science* 235:1173–1178 (1987).

Verspieren, P. et al., "An Acridine-Linked Oligodeoxynucleotide Targeted to the Common 5' End of Trypanosome mRNAs Kills Cultured Parasites" Gene 61: 307–315 (1987).

Meyer, R.B. et al., "Efficient, Specific Cross-Linking and Cleavage of DNA by Stable, Synthetic Complementary Oligodeoxynucleotides" J. Am. Chem. Soc. III 8517–8519 (1989.)

Offensperger et al., "In vivo Inhibition of Duck Hepatitis B Virus Replication and Gene Expression by Phosphorothioate Modified Antisense Oligodeoxynucleotides" EMBO Journal 12: 1257–1262 (1993).

Simons et al., "Antisense c-myb Oligonucleotides Inhibit Intimal Arterial Smooth Muscle Cell Accumulation In Vivo" Nature 359: 67–70 (1992).

Burch et al., "Oligonucleotides Antisense to the Interleukin 1 Receptor mRNA Block the Effects of Interleukin 1 in Cultured Murine and Human Fibroblasts and in Mice" J. Clin. Inves. 88: 1190–1196 (1991).

Kitajima et al., "Ablation of Transplanted HTLV-1 Tax-Transformed Tumors in Mice by Antisense Inhibition of NF-κB" Science 258: 1792–1795 (1992).

Higgins et al., "Antisense Inhibition of the p65 Subunit of NFκB Blocks Tumorigenicity and Causes Tumor Regression" Proc. Natl. Acad. Sci. USA 90: 9901–9905 (1993).

Alberts et al eds. Molecular Biology of the Cell 2nd ed. pp. 56–57.

Antiviral Agents Bull. vol. 5 No. 6: 161–163 (1992).

BioWorld Today, p. 3 of 4 Dec. 20, 1993.

Modak et al., "Toward Chemical Ribonucleases. 2. Synthesis and Characterization of Nucleoside-Bipyridine Conjugates. Hydrolytic Clearate of RNA by Their Copper(II) Complexes" JACS 113: 283–291 (1991).

Chin et al., Co(III) Complex Promoted Hydrolysis of Phosphate Diesters: Comparison in Reactivity of Rigid cisDiaquotetraazacobalt(III) Complexes" JACS 111: 186–190 (1989).

Westermann et al., "Inhibition of Expression of SV40 Virus Large T-Antigen by Antisense Oligodeoxyribonucleotides" Biomed. Biochim. Acta 48: 85–93 (1989).

Moldave, "Eukaryotic Protein Synthesis" Ann Rev. Biochem. 54: 1109–1149 (1985).

Moss, "Chapter 5: 5' Terminal CAP Structures of Eukaryotic and Viral mRNAs" Processing of RNA, Apirion, Ed. CRC Press, Inc. Boca Raton, Florida (1984).

A) 5' Capped RNA Target

5' m⁷GpppGAGCUCCUCUGCUACUCAGA³²pCp 3'

B) Anti-Sense Oligodeoxynucleotide

IP7399-MAG

3' T G*G* CTCGAGGAGACGATGAGTCT 5'

C) Modified Base Structure

G* = N2-(MAG)G

G*:Cu(H) = N2-[MAG:Cu(H)]G

COMPOSITIONS AND METHODS FOR MODULATING RNA ACTIVITY THROUGH MODIFICATION OF THE 5' CAP STRUCTURE OF RNA

This application is a continuation-in-part of U.S. patent application Ser. No. 07/847,054, filed on Apr. 3, 1992, now abandoned.

FIELD OF THE INVENTION

This invention is directed to modification of the 5' cap structure of RNA using nucleic acid complementary to the 5' end of a messenger RNA to effect alteration of the 5' cap structure of the RNA, thereby modulating its function. Thus, the invention generally relates to gene expression in animal cells, and to protein expression in particular.

BACKGROUND OF THE INVENTION

The 5' cap of eukaryotic and viral messenger RNAs (mRNAs) is a structurally and chemically unique entity located at the 5' terminus of RNAs. It plays a pivotal role in mRNA metabolism, and is required to varying degrees for processing and maturation of the transcript in the nucleus, transport of the message from the nucleus to the cytoplasm, mRNA stability, and efficient translation of message to protein. The 5' cap structure provides resistance to 5'-exonuclease activity, and its absence results in rapid degradation of the mRNA.

Based upon current understanding of the physical and chemical properties of the 5' cap of mRNA, it is believed that its structural or chemical modification leads to the modulation of mRNA expression. Reagents that alter or cleave the 5' cap of mRNA are desirable in the preparation of cDNA libraries where the presence of excessive amounts of some mRNAs make analysis of the less abundant mRNAs difficult and tedious. By altering or cleaving the 5' cap of overabundant mRNAs, those that occur in much lower abundance can be isolated and analyzed.

Selective degradation of a specific mRNA, leading to its inactivation, is of significant utility in the identification and study of the cellular function of that mRNA. Compositions that alter or cleave the 5' cap of mRNAs are desired for their use in distinguishing among the cellular functions of closely related mRNAs.

It is well known that most of the bodily functions in mammals including most disease states, are effected by proteins. Classical therapeutics have generally focused upon interactions with such proteins in efforts to moderate their disease causing or disease potentiating functions.

Recently, attempts have been made to selectively moderate the actual production of such undesired proteins by interactions with molecules that direct their synthesis, intracellular RNA. These interactions involve the binding of complementary "antisense" oligonucleotides or their analogs to the intracellular RNA in a sequence specific fashion by Watson-Crick base pairing interactions. Intracellular hybridization of the two molecules is intended to inhibit either the synthesis and proper metabolism of the selected mRNA or its utilization by the translational machinery in the synthesis of proteins. It is believed that interference with the production of proteins in this manner would yield a therapeutic effect with minimal side effects due to the high level of reaction specificity available through RNA sequence recognition by the antisense molecules [*Cancer Res.* 48 2659–68 (1988); *Pharmaceutical Res.* 5 539–49 (1988); *Anticancer Drug Design* 2 117–128 (1987)].

Several chemical modifications have been introduced into oligonucleotides to increase their therapeutic activity [*Nucleic Acid Research* 6 3009–24 (1979); *Biochemistry* 18 5134–43 (1979); *Journal of the American Chemical Society* 111 2321–22 (1989); *Proc. Natl. Acad. Sci. USA* 85 7079–7083 (1987); *Biochemistry* 27 7237–46 (1986), *Nucleic Acid Research* 14 3487–99 (1986); *Nucleic Acid Research* 15 4717–36 (1987); *Biochemistry* 27 3997–4003 (1988); *Nucleic Acid Research* 15 8643–59 (1987); *Acc. Chem. Res.* 19. 180–86 (1986).

There is a significant body of published literature that demonstrates the therapeutic utility of antisense oligonucleotides [*EMBO Journal* 12 1257–1262 (1993); *Nature* 359 67–70 (1992); *J. Clinical Investig.* 88 1190–1196 (1991); *Science* 258 1792–1795 (1992); *Proc. Natl. Acad. Sci. USA* 90 9901–9905 (1993)]. These references evidence the fact that oligonucleotides can be administered to an animal in vivo, and when so administered an oligonucleotide can be effective in alleviating or diminishing the disease state to which it is directed. It is generally accepted that a clear correlation exists between results obtained by in vitro determination of the ability of specific oligonucleotides to modulate the expression of targeted genes and the activity of the oligonucleotides in vivo.

Published literature also indicates that oligonucleotides have been approved for clinical trials and are being administered to human patients [*Antiviral Agents Bulletin* 5 161–163 (1992); *BioWorld Today*, Dec. 20, 1993]. They are known not to have unacceptable toxicity in dosages required for therapeutic use.

Oligonucleotide compositions capable of masking, modifying or cleaving the 5' cap of mRNA are desired as therapeutic agents, and are expected to satisfy the long-felt need for effective therapeutic modalities with either few or no side effects.

SUMMARY OF THE INVENTION

In accordance with the present invention, compositions for modulating the activity of RNA are provided. These compositions comprise a reactive portion capable of chemically or structurally masking, altering or removing the 5' cap structure of a targeted RNA. The composition further provides a targeting portion which is specifically hybridizable with the 5' terminal region of a targeted RNA for placement of the reactive portion in a reactive position for the 5' cap. The compositions also include a tether portion for connecting the targeting and reactive portions to each other.

In accordance with one embodiment of the invention, the reactive portion of the composition comprises one or more functionalities capable of catalytically removing or catalytically modifying the 5' cap of messenger RNA.

In other preferred embodiments, the reactive portion of the composition comprises one or more functionalities capable of chemically or structurally masking, modifying or removing the 5' cap of messenger RNA in a non-catalytic manner. Such functionalities may be nucleophilic, electrophilic, basic, acidic, cationic, amphoteric, or redox active for such purposes. Specific examples of such moieties include imidazole, N-methylimidazole, histamine, pyridine, 1,5,9-triazacyclododecane, diethylene triamine, triethylene tetramine, and zinc(II), copper(II) or lanthanide metal complexes of 1,10-ortho-phenanthroline, bipyridine or oligonucleotides that are specifically hybridizable with the 5' terminal region of target mRNA. Of these, triethylene tetramine is preferred, and the copper(II) and lanthanide metal complexes even more preferred.

In accordance with preferred embodiments, the targeting portion of this invention comprises an oligonucleotide (or analog) from 5 to 50 base units in length which recognizes the 5' terminal region of the targeted transcript. It is not necessary that the targeting portion bind to the absolute 5' end of the targeted mRNA, but may bind to a target site beginning one or more nucleotides downstream from the cap itself. Compositions whose targeting portion bind to regions downstream from the cap are comprehended by this invention provided that such compositions are able to achieve the desired effect of masking, modification or cleavage of the 5' cap. It is presently preferred, however that the targeting portion binds to sequences beginning with nucleotides at positions 1 to 50, and more preferably positions 1 to 20, at the 5' end of the mRNA, and proceeding downstream (toward the 3' end of the mRNA target). Position 1 is defined as the first nucleotide adjacent to the 5' cap structure.

The targeting portion is preferably an analog of an oligonucleotide wherein at least some of the oligonucleotide has been substituted with a structure which functions to enhance the ability of the compositions to penetrate into the intracellular region of cells where the RNA whose activity is to be modulated is located and to provide nuclease resistance. In accordance with one preferred embodiment, the oligonucleotides and oligonucleotide analogs are formulated such that at least some of the linking groups between nucleotide units of the oligonucleotide comprise sulfur-containing species such as phosphorothioate moieties.

The tether portion of the composition comprises functionalities which will optimize the placement of the reactive portion with respect to the targeting portion for removal or modification of the 5' cap structure. Such functionalities may have specific hydrogen donor and acceptor capabilities and motifs for optimal placement of the reactive portion. In one embodiment the tether comprises one or more nucleotides. In another embodiment the tether comprises one or more amino acids.

In one preferred embodiment, the compositions of the invention mask the 5' cap of the mRNA such that binding of one or more 5' cap-specific binding proteins, such as eIF-4E, is modulated.

The invention is also directed to methods for modulating the production of a protein by an organism comprising contacting the organism with a composition formulated in accordance with the foregoing considerations. It is preferred that the targeted RNA sequence be preselected to comprise that portion of RNA, preferably messenger RNA, which codes for the protein whose formation is to be modulated, inhibited or arrested. The targeting portion of the composition to be employed is, thus, selected to be complementary to the preselected sequence of RNA.

This invention is also directed to methods for treating an organism having a disease characterized by the undesired production of a protein comprising contacting the organism with a composition in accordance with the same preferable considerations as given in the previous paragraph.

BRIEF DESCRIPTION OF THE DRAWINGS

FIG. 5A shows the sequence of the target mRNA; FIG. 5B shows the sequence of the oligonucleotide-MAG:Cu(II) conjugate; and FIG. 5C shows the structure of MAG:Cu(II) attached to deoxyguanosine.

DETAILED DESCRIPTION

Figure 1:
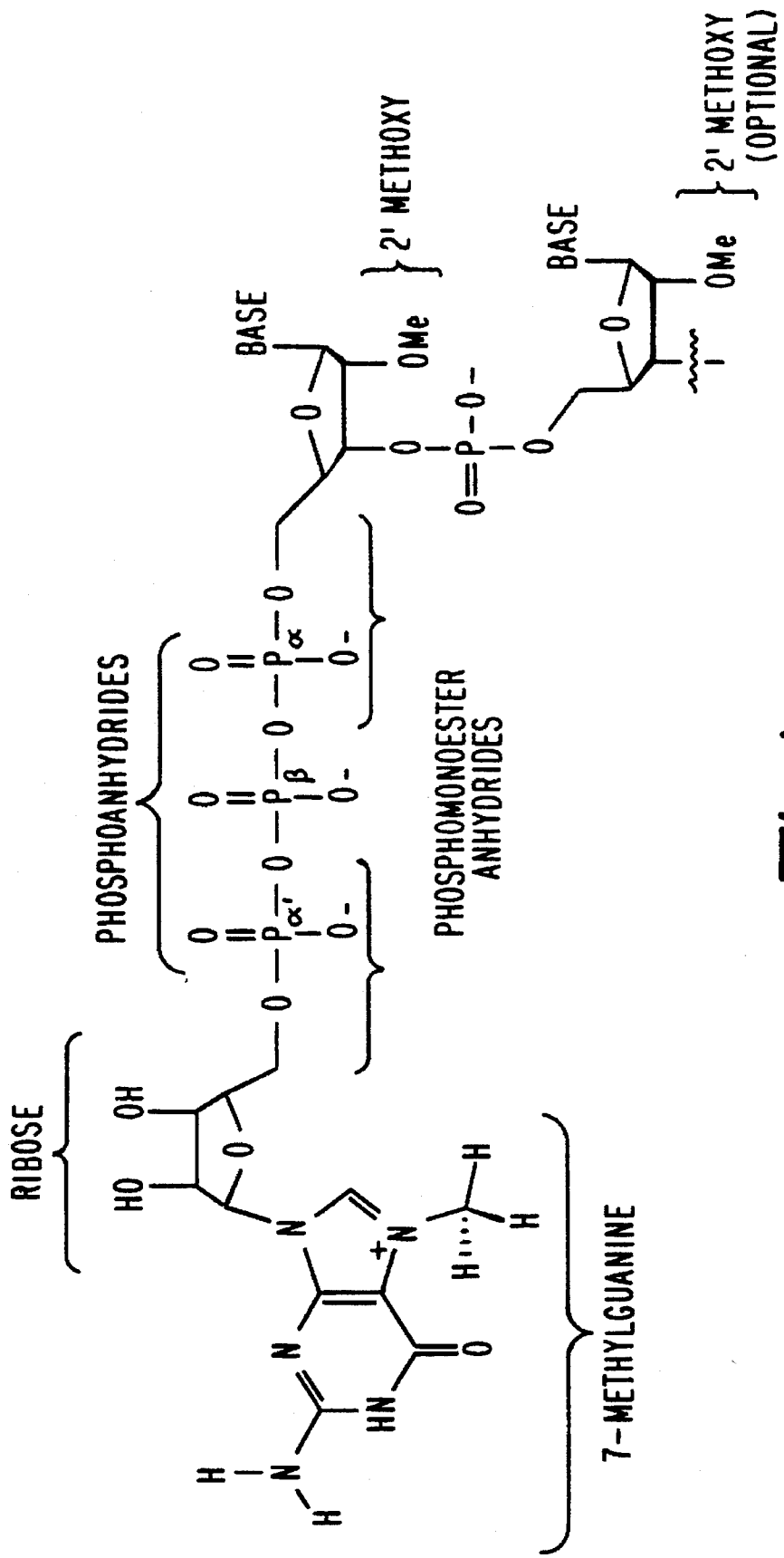
FIG. 1 depicts the structure of the 5' cap of an mRNA.

It has been recognized that the majority of eukaryotic and viral small nuclear RNAs and messenger RNAs have a unique chemical structure at their 5' terminus which is required in varying degrees for their maturation, stability, and efficacy in translation. The general structural features of the 5' cap are given in *J. Mol. Biol.* 99 519–547 (1975) and are shown in FIG. 1. The cap comprises a guanosine residue which is methylated at the nitrogen 7 position. This residue is joined to the penultimate 5' base of the RNA via a triphosphate linkage between the 5' hydroxyl groups of each residue. The 2' hydroxyl groups of the 5' terminal base(s) are methylated.

The 5' cap structure of small nuclear RNA differs from that of mRNA in that caps on small nuclear RNAs are dimethylated at the exocyclic amino group of the guanine residue, whereas the 5' cap of mRNA features a guanosine residue methylated at the N7 (endocyclic) position. This feature on small nuclear RNAs is believed to be an important determinant of the functional destiny of small nuclear RNAs versus mRNAs [*Nucleic Acid Research* 16 8953 (1988)]. The cap structure on mRNAs is added to nascent transcripts during transcription in the nucleus. Once transcribed, the primary transcript of both eukaryotic and certain viral genes require processing to remove intervening sequences (introns) within the coding regions of the transcript. It is well established that the 5' cap is necessary for processing of primary transcripts to mature RNA molecules, specifically for the splicing reactions which effect removal of the introns [*Cell* 38 731–736 (1984)]. Absence of a 5' cap on an mRNA results in rapid degradation of the RNA in the nucleus and the cytoplasm [*Mol. Biol. Med.* 5 1–14 (1988) and *Cell* 32 681–694 (1983)]. The majority of eukaryotic and viral mRNAs studied to date require the presence of a 5' cap for initiation of translation [*Cell* 9 645–653 (1976); *Federation of Experimental Biologists Society Letter* 96 1–11(1978); *Prog. Nuc. Acid Res.* 35 173–207 (1988)]. There are also specific cap binding proteins which are components of the machinery required for initiation of translation of an mRNA [*Cell* 40 223–24 (1985); and *Prog. Nuc. Acid Res.* 35 173–207 (1988)]. Based on the current understanding of the properties and function of the 5' cap structure on mRNA, it is now believed that certain modifications of the structure, such as removal thereof or structural or chemical alterations thereon, will affect the function of the transcript. Oligonucleotides may provide such a disruption of mRNA function.

Compositions that cleave the 5' cap of desired mRNAs are useful as research reagents. They may be used for degrading specific mRNAs from a mixture of mRNAs, or may have utility in distinguishing among the cellular roles of closely related mRNAs.

Compositions that remove the 5' cap of specific target mRNA are useful as research reagents. Removal of the 5' cap inactivates the mRNA molecule and eventually leads to its degradation [*Mol. Biol. Med.* 5 1–14 (1988)]. Therefore, cap removal is useful for inactivating specific mRNAs from a mixture of mRNAs. One such application is in the preparation of optimized cDNA libraries. cDNA libraries are prepared by isolating mRNA from the desired cells or tissue, synthesizing the corresponding double-stranded cDNAs, and cloning the cDNAs into the desired vectors for maintenance and experimentation. A common problem encountered is overabundance of a particular undesired message in the library. In many cells or tissues, a particular mRNA species represents the vast majority of the total mRNA. For example, abundant mRNAs such as those encoding globin, immunoglobulins and ovalbumin may constitute as much as 50–90% of the total poly(A)+ cytoplasmic RNA isolated from certain cell types [Sambrook et al. (1989) *Molecular Cloning. A Laboratory Manual*, 2nd edition, Cold Spring Harbor Laboratory Press, Volume 2, pg. 8.6]. Other mRNAs which encode non-structural proteins such as regulatory proteins and the like are present in much lower abundance, often a fraction of one percent; such rare mRNAs are difficult to analyze because of their vast underrepresentation in cDNA libraries. Inactivation and degradation of the overabundant mRNA species leads to a proportional increase in the representation of the rare messages in the library. Compositions of the present invention which specifically cleave the overabundant mRNA are, therefore, useful as research reagents.

Inactivation and degradation of a specific mRNA is also useful for examining the respective roles of closely related mRNAs or their encoded proteins. Because of the extreme specificity of oligonucleotide binding to its target, and in view of the fact that nucleotide sequences in the 5' cap region are not highly conserved even among related proteins, it is possible using the compositions of the invention to inactivate or modulate the function of a particular target mRNA in a mixture of several mRNAs encoding very similar proteins. For example, ICAM-1 and VCAM-1 are cellular adhesion molecules which are expressed on vascular endothelium. Both of these molecules are involved in the inflammatory response process and both mediate adhesion of white blood cells to vascular endothelium and other cell types. Expression of both VCAM-1 and ICAM-1 is induced by cytokines. A reagent which specifically inactivates and degrades ICAM-1 mRNA in cultured endothelial cells is useful for the analysis and elucidation of the roles played by both ICAM-1 and VCAM-1 in these cells.

In general, the compositions necessary for modulating the activity of an RNA transcript in accordance with this invention may be regarded in three portions: the reactive moiety, the tether, and the antisense targeting portion.

The function of the reactive moiety is to mask, modify or remove by cleavage the 5' cap of the targeted transcript such that the transcript is unable to operate in one or more of its normal processes beginning from the time of synthesis of the 5' cap structure on the targeted mRNA to the time of degradation and removal of the targeted transcript from the intracellular translation pool.

The function of the tether is to link the reactive moiety and the antisense targeting portion. The tether may include organic and/or inorganic functional groups which optimize the position and orientation of the reactive moiety to achieve the utmost precision in specific activity towards removal or modification of the 5' cap. The tether of the oligonucleotide compositions of this invention preferably comprises from about 1 to about 500 atoms. It is more preferred that such tethers comprise from about 1 to about 50 atoms.

The antisense targeting portion is an oligonucleotide or oligonucleotide analog that has a nucleotide sequence complementary to the 5' end region of target mRNA, and its function is to direct the reactive moiety specifically to the 5' terminal region of the targeted transcript, preferably without interference in non-targeted cellular processes and in a manner which facilitates the functional ability of the reactive moiety and tether. The oligonucleotides in accordance with this invention preferably comprise from about 5 to about 50 nucleotides. It is more preferred that such oligonucleotides comprise from about 8 to about 25 nucleotides.

Each aspect of the 5' cap structure can be exploited singly or together as required to achieve the objectives of this invention. These include phosphoanhydride linkages, phosphomonoester anhydride linkages, methylated guanine residue and its appended ribose residue. Examples of experimental means which address each aspect follow.

Figure 2:
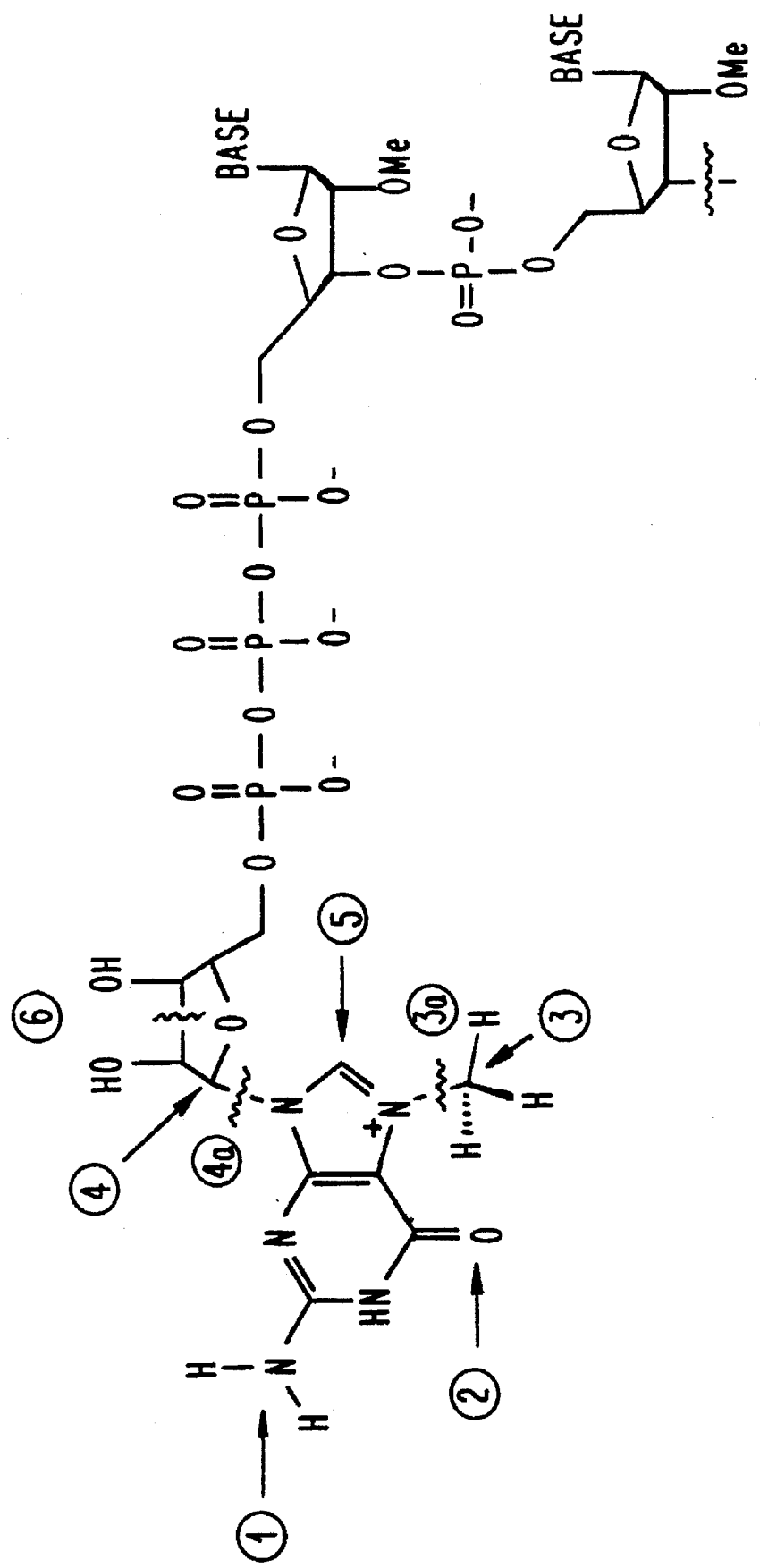
FIG. 2 depicts potential sites for chemical attack on the methylated guanosine residue of the 5' cap structure of mRNA.
Figure 3:
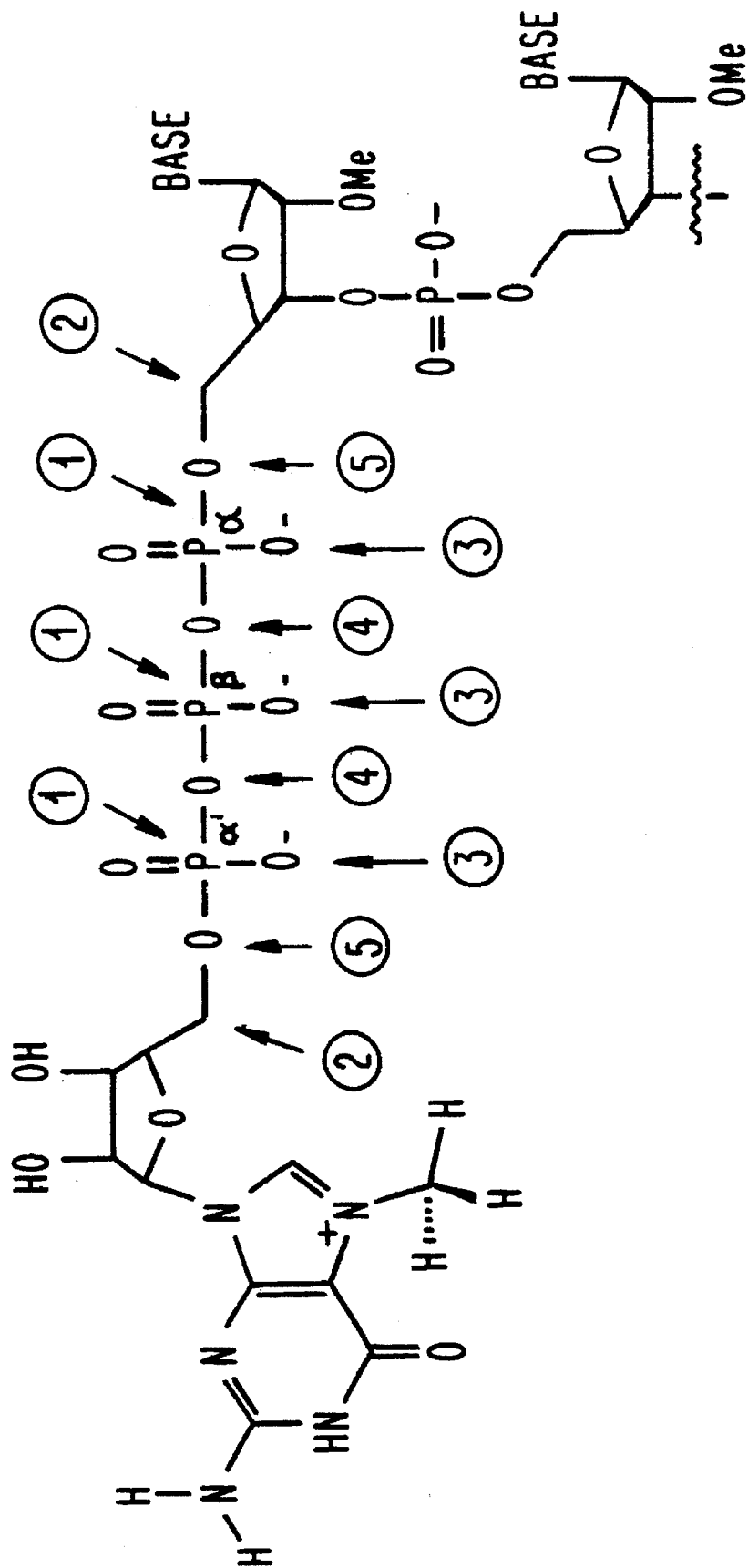
FIG. 3 shows potential sites for chemical attack on the triphosphate linkage of the 5' cap structure of mRNA.

FIGS. 2 and 3 depict the reactive atoms and bonds of the 5' cap structure which, because of their inherent chemical nature, are susceptible to modification or cleavage given the appropriate reactive moiety.

FIG. 2 displays sites of the methylated guanine residue and its appended ribose residue which are viable targets for modification of the 5' cap structure. Both the exocyclic nitrogen at the 2 position (site 1) and the oxygen at the 6 position (site 2) of the methylated base are nucleophiles. Therefore, they may be modified via alkylation utilizing functional groups such as sulfonyl alkyl halides, alpha-halo carbonyls, or aziridines.

Both the nitrogen methyl bond (site 3a) and the nitrogen-glycosidic bond (site 4a) are labile due to the electron deficient state of the aromatic ring. Therefore, nucleophilic attack at the 7-methyl carbon (site 3) or carbon one of the ribose (site 4) would result in cleavage of the nitrogen carbon bond to yield an aberrant cap structure. Reactive groups include amines, hydroxyls, and sulfhydryls.

The carbon at the 8 position of the methylated guanine residue (site 5) is electrophilic due to the methylated, and consequently electropositive, nitrogen at position 7. Therefore, this site is amenable to reactions with nucleophilic groups such as amines and hydroxyls.

Cleavage of the bond between carbon 3 and carbon 4 of the sugar ring (site 6) may be achieved oxidatively via the 2' and 3' hydroxyl groups utilizing reactive moieties such as chelated metals.

FIG. 3 indicates those sites of the phosphate chain which are viable targets for the modification and removal of the 5' cap structure utilizing nucleophiles and/or electrophiles as reactive groups.

Both the phosphorus atoms (site 1) and the carbon 5 atoms (site 2) are amenable to attack by a nucleophile. Nucleophilic attack would result in displacement of one of the attached intrachain oxygen atoms and thus cleavage of the phosphoanhydride chain between the penultimate base of the mRNA and the methylated guanosine. These reactions can be catalytic given the appropriate choice of nucleophile (e.g. amines and carboxylates).

The oxygen atoms at sites 3, 4, and 5 are all sites for enhancement or activation of the catalytic cleavage reactions by nucleophiles (at sites 1 and 2) via protonation or metal interactions using additional functional groups appended to the tether. In addition these oxygens are susceptible to electrophiles and thus alkylation which would result in irreversible modification of the phosphoanhydride linkage.

The reactive moiety of a composed therapeutic molecule can be a composite itself with multiple functional groups to achieve the desired reaction or simply one functional group to do the same. As exemplified previously, single entities available include nucleophiles, e.g., amines, and hydroxides via coordination chemistry; Lewis or Brönsted acids and bases, including metals; and redox active functional groups, e.g., chelated metals.

One of several plausible means for catalytic removal of the 5' cap involves utilization of pyridine as the reactive moiety. Pyridine, acting as a nucleophile, is capable of cleaving exclusively pyrophosphate diesters in the presence of phosphodiesters under aqueous conditions [*Can. J. Biochem.* 50 287–291 (1972)]. This type of nucleophile, an aromatic nitrogen, cleaves the pyrophosphate bond via a covalent intermediate. The intermediate is then hydrolyzed to release the cleaved product and the reactive nucleophile. It is thus a catalytic reaction.

Pyridine can be tethered by known synthetic methodologies [*Organic Chemistry*, Vol. 19, A. R. Katritzky and J. M. Lagowski (1971)], from one of several sites on its aromatic ring to an antisense oligonucleotide. Such an attachment is intended to place the reactive pyridinic nitrogen in close and reactive proximity to one of the electrophilic phosphorus or carbon atoms of the 5' cap. As an example, attachment of a variety of substituents to the 4 position of the aromatic ring may be accomplished via the N-oxide derivative of pyridine. This compound is derived from the reaction between pyridine and peracetic acid. Reaction upon the N-oxide via either electrophilic (nitration) or nucleophilic reaction mechanisms (alcohols, amines, halogens, sulfhydryls, or organometallic groups) will generate pyridine derivatives appropriately functionalized, e.g., with an amine or a carboxylic acid, for the attachment to the antisense binding unit.

The advantage of pyridine as a nucleophile, in the case of the phosphorus atoms, is that it is neutral and thus will experience nominal electrostatic interference from the anionic phosphate oxygens [*Science* 235 1173–1178 (1987)]. Based on the $pK_a$ values of the nucleoside mono, di, and triphosphates and the relationship of $pK_a$ to the leaving group ability in nucleophilic displacement reactions it is believed that it is preferred to place a nucleophile in an optimal position for nucleophilic attack on the β-phosphorus atom of the 5' cap linkage.

In addition to pyridine, other organic alkyl and aromatic amines are provided which act as nucleophiles, Lewis acid/bases or general acid/bases and which cause chemical alteration of the 5' cap. Imidazole, N-methylimidazole, histamine, 1,5,9-triazacyclododecane, diethylene triamine and triethylene tetramine were all shown to react with the 5' cap structure. It is presently believed that the reaction of these amines upon the 5' cap causes hydrolysis of the 7-methylguanosine residue.

In addition to the amines, metal complexes are provided that have been found to be effective in chemical removal (cleavage) of the 5' cap. Copper(II) and zinc(II) complexes of the chelators 1,10,-ortho-phenanthroline and bipyridine are even more reactive upon the 5' cap structure than are the alkyl and aromatic amines. Of these four metal complexes, the copper(II)-ortho-phenanthroline complex was most reactive. It is presently believed that this complex reacts with the 5' cap to cause hydrolysis of the phosphoanhydride linkage in a non-catalytic manner.

Other metal complexes of utility in cleavage of the 5' cap are lanthanide complexes such as Pr:DTPA-dien (DTPA= Diethylenetriaminepentaacetic acid), Eu:DTPA-dien, Yb:DTPA-dien, Eu:THED (THED=1,4,7,10-tetrakis(2-hydroxyethyl)-1,4,7,10-tetraazacyclododecane), Eu:THP (THP=1,4,7,10-tetrakis(2-hydroxypropyl)-1,4,7,10-tetraazacyclododecane), La:TCMC (TCMC=1,4,7,10-tetrakis(2-carbamoylmethyl)-1,4,7,10-tetraazacyclododecane), $EuCl_3$, and Co:Trien.

Of the metal chelators provided, Eu:DTPA-dien, Eu:THED, $EuCl_3$ and Co:Trien are preferred, and have demonstrated 5' cap cleavage of target mRNA. After 25 hours at 37° C., Eu:DTPA and Co:Trien complexes yielded 47% and 42%, respectively, of cleaved RNA products, whereas Eu:THED demonstrated 90% cap cleavage at the end of 4 hours at 37° C. Cu(II) complex of N-(2-mercaptopropionyl)glycine (MPG) has also proven effective for cleavage of the 5' cap structure of target mRNA. MPG:Cu(II) demonstrates 25% cleavage of the cap structure at a concentration of 0.15 mM, and at a concentration of 1.5 mM the said complex demonstrates 56% cap cleavage.

Figure 5:
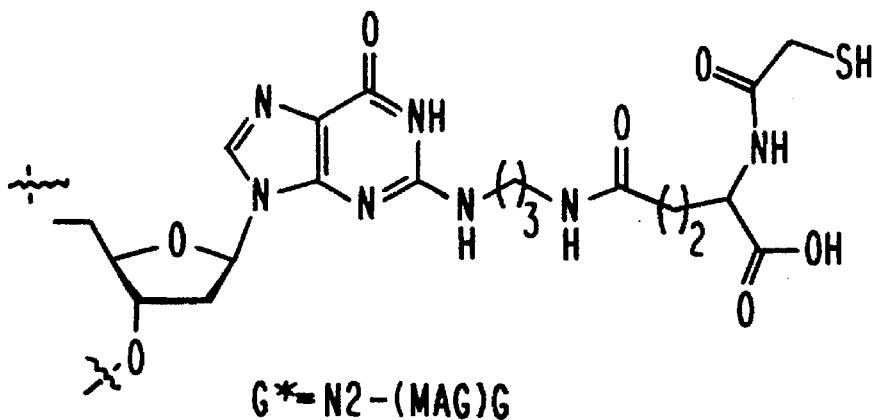
FIGS. 5(A–C), comprising parts A, B and C, shows the structure of oligonucleotide-MAG:Cu(II) conjugate and the sequence of its RNA substrate.
Figure 5:
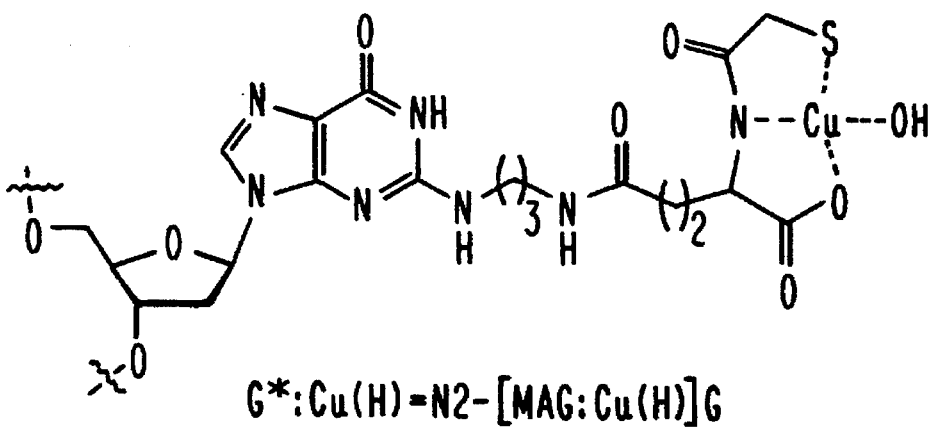

Further, these cap cleaving metal complexes may be attached to oligonucleotides specifically hybridizable with target mRNA in order to cause 5' cap cleavage of the mRNA. This provides increased specificity of the cleaving reactive moiety for the target RNA. Use of one such metal complex, Cu(II) complex of IP7399-MAG, has resulted in decapitation of the 5' cap of a 3' radiolabeled RNA substrate, and its structure and sequence are shown in FIG. 5.

The reactive moiety of an oligonucleotide composition is also capable of masking the 5' cap structure of mRNA, thereby interfering with the function of the RNA. "Masking", in the context of this invention, refers to steric, electronic or other interference with the 5' cap structure, so that the cap is blocked from performing one or more of its normal functions. For example, the 5' cap of RNA functions as a recognition moiety for proteins involved in RNA metabolism. One such protein that has been shown to play a role in the initiation of translation is the eukaryotic initiation factor 4E (eIF-4E) [Rhoads, R. E. *Trends Biochem. Sci.* 13 52–56 (1988); Sonenberg et al. *Proc. Natl. Acad. Sci. USA* 75 4843–4847 (1978)], which binds specifically to the 5' cap of mRNA. Inhibition of this binding event results in the modulation of mRNA activity. The availability of eIF-4E permits the development of 5' cap-specific antisense oligonucleotide chemistry by the utilization of a mechanism-based method for analyzing the efficiency of the oligonucleotide composition in inhibiting the binding of eIF-4E to mRNA. The evaluation of the ability of the cap to bind isolated eIF-4E is one means of evaluating and determining whether the 5' cap structure is masked, modified or removed. eIF-4E binding can be measured by gel-shift assay using methods known in the art.

The detailed placement of the reactive moiety is governed by the tether or linker between it and the antisense binding unit. The length of the tether may be anywhere between 1 and 500 atoms, or more preferably between 1 and 50 atoms, excluding any additional appendages, e.g., functional groups appended to the main chain of the tether.

Preferred means of attachment of the tether to the antisense binding unit are via ethers, esters, or amides from the sugar or phosphate residue of the penultimate base of the antisense strand. Attachments may also be effected on the penultimate base, e.g., the 5 position of the pyrimidines. In addition, attachments may be made to the 2 position of the penultimate base in the case of purines. In one embodiment the tether comprises one or more amino acids. In another embodiment the tether comprises one or more noncomplementary natural or modified nucleotides. As shown in Example 6, the presence of two extra "dangling" bases extending off the 3' end of an antisense oligodeoxyribonucleotide (opposite the 5' cap of the RNA) does not inhibit specific hybridization of the antisense oligonucleotide to a 5'-capped RNA. Thus, tethers such as those described above are unlikely to affect the ability of the oligonucleotide to hybridize to the target mRNA sequence.

Figure 4:
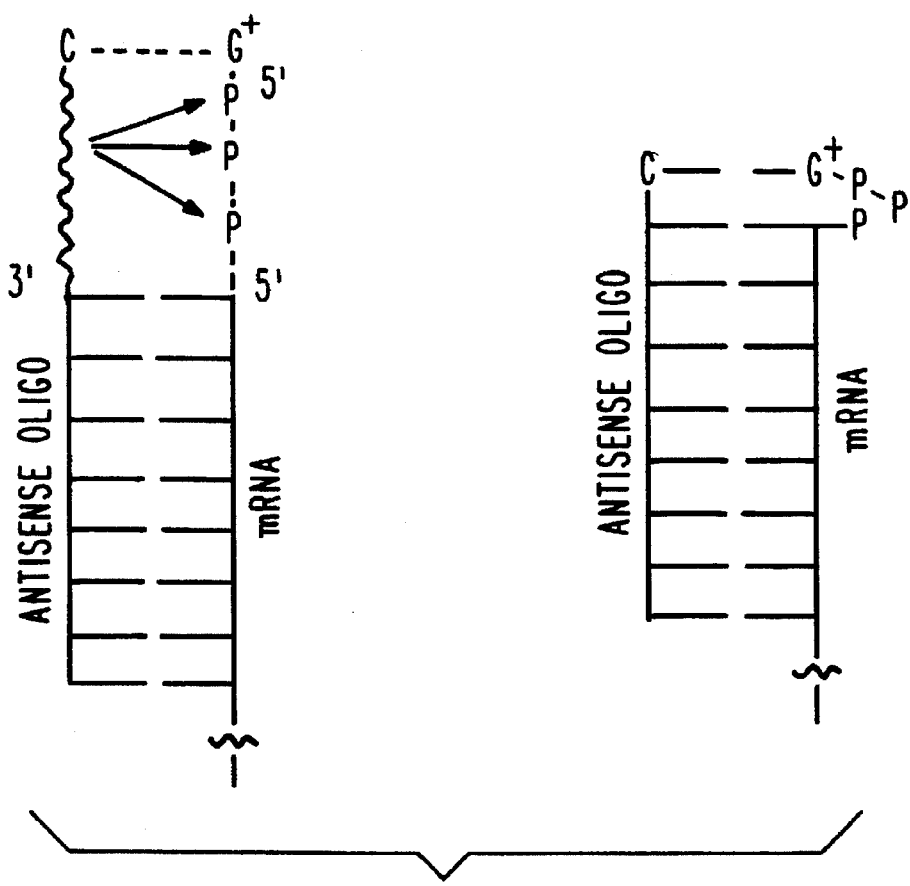
FIG. 4 depicts two approaches to utilization of cytosine as an appendage or anchor to the tether to enhance placement of the reactive moiety.

Appendages to the tether may include additional binding units, such as a cytosine residue or a guanidinium group, which are specific to the 5' cap structure, such as the methylated guanosine residue or the anionic phosphate groups respectively. FIG. 4 shows a set of examples for a cytosine appendage. The intent is to add an additional binding element to further constrain or fix the conformation of the 5' cap. Additionally, it may provide an avenue for improved placement (or anchoring) of a catalytic cleavage moiety, such as a nucleophile, next to the alpha or beta phosphorus atoms of the cap linkage. The cytosine may be attached via a specialized tether, in length or composition, or via one of the known phosphate linkages.

The next portion of the composition to be considered, is the complementary nucleotide binding unit. This portion of the molecule is that which positions the reactive moiety onto the selected mRNA to be modified. In the present invention, the complementary nucleotide binding unit specifically positions each of the components of the molecule to the 5' region of the selected transcript in reactive proximity to the 5' cap structure.

The targeting portion of the composition is generally either an oligonucleotide or oligonucleotide analog. It is designed and synthesized, generally through solid state synthesis, solution phase synthesis or enzymatic synthesis of known methodology. Nucleic acid synthesizers and relevant enzymes are commercially available, the use of which is generally understood by persons of ordinary skill in the art. The available methodologies are capable of generating nearly any oligonucleotide of reasonable length which may be desired.

In the context of this invention, the term "oligonucleotide" refers to a plurality of joined nucleotide units formed from naturally-occurring bases and furanosyl groups joined by native phosphodiester bonds. This term effectively refers to naturally-occurring species or synthetic species formed from naturally-occurring subunits.

"Oigonucleotide analog," as the term is used in connection with this invention, refers to oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Specific examples of some preferred oligonucleotide analogs envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form or "universal base" such as inosine. Persons of ordinary skill in the art will be able to select other linkages for use in the practice of the invention.

Such analogs are best described as being functionally interchangeable with natural oligonucleotides (or synthesized oligonucleotides along natural lines), but which have one or more differences from natural structure. All such analogs are comprehended by this invention so long as they function effectively to specifically hybridize with the RNA molecule bearing the 5' cap to be structurally or chemically modified.

It is preferred in some embodiments of the present invention to employ oligonucleotide analogs rather than the oligonucleotides themselves. In this context, oligonucleotide analog refers to structure which is generally similar to native oligonucleotides in its ability to complex with the sense strand. Modifications include those that enhance the ability of the antisense molecule to penetrate into the intracellular spaces of cells where the targeted messenger RNA resides and those modifications which provide nuclease resistance. For these purposes it is currently preferred to substitute modified backbones, non-ionic, non-chiral or enantiomerically pure entities, in place of some or all of the phosphodiester bonds. Modifications may also include those that enhance the attachment and/or placement of the tether and reactive moiety in order to achieve optimal reactivity with the 5' cap. To achieve this goal alpha-anomeric oligonucleotides which will bind parallel (5'-3':5'-3') to the 5' terminal sequence of the targeted transcript can be used. Any of the existing or to be discovered methods for accomplishing these goals may be employed in accordance with the practice of the present invention. The targeting portions of the compositions of the present inventions, are preferably oligonucleotides or oligonucleotide analogs having about 5 to about 50 base units, or base analogs. It is more preferred that such functionalities have about 8 to 25 base units.

The present invention employs oligonucleotide compositions specifically hybridizable to the 5' terminal region of target mRNA. This relationship between an oligonucleotide and the complementary nucleic acid target to which it hybridizes is commonly referred to as "antisense."

In the context of this invention, "modulation" means either inhibition or stimulation of gene expression. Inhibition of specific mRNA expression is presently the preferred form of modulation.

"Hybridization," in the context of this invention, means hydrogen bonding, also known as Watson-Crick base pairing, between complementary bases, usually on opposite nucleic acid strands or two regions of a nucleic acid strand.

Guanine and cytosine are examples of complementary bases which pair with each other through the formation of three hydrogen bonds. Adenine and thymine are also examples of complementary bases which pair through the formation of hydrogen bonds.

"Complementary," as used herein, also refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, "specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted.

Oligonucleotides have recently become accepted as therapeutic moieties in the treatment of disease states in animals and man. For example, U.S. Pat. No. 5,098,890 is directed to antisense oligonucleotide therapies for certain cancerous conditions. U.S. Pat. No. 5,135,917 provides antisense oligonucleotides that inhibit human interleukin-1 receptor expression. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence with a portion of an oncogene. U.S. Pat. Nos. 5,276,019 and 5,264,423 are directed to oligonucleotide analogs used to prevent replication of foreign nucleic acids in cells. U.S. Pat. No. 4,689,320 is directed to antisense oligonucleotides as antiviral agents specific to CMV. U.S. Pat. No. 4,999,421 is directed to peptides expressed by the antisense strand of HTLV-1. U.S. Pat. No. 5,242,906 provides antisense oligonucleotides useful in the treatment of latent EBV infections.

Offensperger et al. [*EMBO J.* 12 1257–1262 (1993)] disclose a phosphorothioate-modified antisense oligonucleotide directed against duck hepatitis B virus. When administered intravenously to ducks, the oligonucleotide resulted in complete inhibition of virus replication and viral gene expression. Inhibition of virus replication in ducks demonstrated clear correlation with in vitro studies performed in primary duck hepatocytes. No toxicity was evident in either infected or uninfected ducks when treated with the oligonucleotide. These results clearly establish that intravenous administration of antisense oligonucleotides results in cell penetration and is a viable therapeutic modality for the treatment of vital infections.

Simons et al. [*Nature* 359 67–70 (1992)] discuss a phosphorothioate-modified c-myb antisense oligonucleotide that is effective as a suppressor of smooth muscle cell proliferation, both in vitro in smooth muscle cells in culture and in vivo in the carotid artery of rats. The data presented demonstrate efficacy of the oligonucleotide in cell culture and correlation of in vitro efficacy with that observed in vivo.

Burch et al. [*J. Clinical Investig.* 88 1190–1196 (1991)], Kitajima et al. [*Science* 258 1792–1795 (1992)], and Higgins et al. [*Proc. Natl. Acad. Sci. USA* 90 9901–9905 (1993)] disclose antisense oligonucleotides that exhibit in vivo efficacy upon subcutaneous or intraperitoneal injection in mice, and in vitro effectiveness in cell culture. These data also demonstrate that the efficacy of the oligonucleotides in vitro correlates well with that observed in vivo.

Determination of the activity of oligonucleotides in vitro is now accepted as a basis for predictions regarding their in vivo efficacy for the treatment of diseases for which they are designed.

Antisense oligonucleotides have been safely administered to humans and several clinical trials are presently underway. Based on these clinical trials, oligonucleotides are understood to have toxicities within acceptable limits at dosages required for therapeutic efficacy. One such antisense oligonucleotide, identified as ISIS 2105, is presently in clinical trials, and is used as a therapeutic against papillomavirus. Another antisense oligonucleotide, ISIS 2922, has demonstrated efficacy against cytomegalovirus-associated retinitis in human patients [*Antiviral Agents Bulletin* 5 161–163 (1992); *BioWorld Today*, Dec. 20, 1993]. It has, therefore, been established that oligonucleotides are useful therapeutic instrumentalities and that the same can be configured to be useful in regimes for treatment of animals, especially humans.

The oligonucleotide compositions of the present invention may also have potential as agents of therapeutic value, and the examples presented herein establish that oligonucleotides useful in the invention are capable of penetrating cells and exerting potential therapeutic effects in that these oligonucleotides ablated viral infection when administered to virus infected cells. As described in the Examples herein, modified oligonucleotides complementary to the 5' cap region of two mRNAs encoded by cytomegalovirus (CMV), IE-1 and IE-2, were tested for their ability to inhibit human CMV (HCMV) replication using a virus yield reduction assay. Primary human fibroblasts, pretreated with the oligonucleotides, were infected with HCMV and then maintained in the presence of the same oligonucleotides. Two types of oligonucleotides (21-mers) complementary to the 5' terminal sequence of IE-1 and IE-2 transcripts were used. One oligonucleotide was designed to hybridize with CMV RNA specifying IE-1 and IE-2 from the 5' penultimate uridine residue to the adenosine residue 22 nucleotides downstream. The other 21-mer oligonucleotide was shifted by 3 nucleotides in the 5' direction to allow for the attachment of two extra noncomplementary "dangling" nucleotides at its 3' end. The purpose of the latter design was to structurally mask the 5' cap structure by the addition of these "dangling" nucleotides. The results obtained from a virus reduction assay established that the antisense oligonucleotide equipped with 2 extra nucleotides at the 3' end was more effective in reducing virus production (90% reduction in virus yield) than that which did not possess any "dangling" nucleotides (40% reduction in virus yield). These results strongly suggest that oligonucleotides penetrate cells and exert their therapeutic effect, which in this case is the structural masking of the 5' cap.

Similarly, according to this invention, an oligonucleotide that has another type of reactive functionality (e.g., a moiety capable of cleaving the 5' cap structure) added thereto is expected to penetrate cells, specifically hybridize with the mRNA to which it is complementary, and allow the reactive moiety to cleave the 5' cap structure.

While the present invention has been described with specificity in accordance with certain of its preferred embodiments, the following examples serve only to illustrate the invention and are not intended to limit the same.

EXAMPLES

Example 1

Cleavage of m7GpppG by metal complexes and amines:

Several copper complexes, alkyl amines and aromatic amines that were judged to be good candidates for eventual tethering to antisense oligonucleotides were assayed for their ability to chemically modify m7GpppG (Pharmacia LKB Biotechnology), a single guanosine nucleotide capped with the methylated guanosine (m7G) cap structure. This structure is analogous to the 5' cap and first (5'-most) nucleotide, here a guanosine, of an mRNA molecule.

(a) Copper complexes:

Copper(II) complexes of 1,10-ortho-phenanthroline (purchased from Lancaster Synthesis) and bipyridine (Aldrich) were assayed as follows. Copper complexes (50–500 µM) and m7GpppG (50–500 µM) were combined in 20 mM HEPES buffer (pH 7.1) in 1.7 mL Eppendorf tubes at reaction volumes of 300 µL. Varying concentrations were used to determine the best ratio of copper complex to substrate. Reactions were carried out at 37° C. for 24 hours, with centrifugation and remixing at 6–8 hour intervals.

(b) Alkyl and aromatic amines:

Imidazole, N-methylimidazole, histamine, pyridine, 1,5,9-triazacyclododecane, diethylene triamine and triethylene tetramine (all purchased from Aldrich) were assayed as follows. 500 mM amine and 1 mM m7GpppG were combined in 0.65 mL Eppendorf tubes at a total reaction volume of 20 µL. Reactions were carried out at 60° C. for 12 hours, with centrifugation and remixing every hour to minimize concentration fluctuation due to evaporation and condensation.

Example 2

Analysis of reactions by anion exchange chromatography:

An aliquot of each reaction was removed at each specified time interval for chromatographic analysis. Injection samples were prepared by addition of the internal standard, nicotinamide adenosine diphosphate (NAD, purchased from Boehringer Mannheim), and dilution to a final volume of 110 µL with double distilled water. Prepared samples were then injected into a 100 µL injection loop and subsequently loaded onto a Pharmacia LKB FPLC (Fast Protein Liquid Chromatography) system utilizing a MonoQ HR 5/5 anion exchange column. Solvent A: distilled water. Solvent B: 1M NaCl plus 5 mM Na Phosphate (pH 7.0). Program gradient: 0 to 40% B in 30 minutes, 40% B for 1 minute, 40% to 100% B in 1 minute, 100% B for 1 minute, 100% to 0% B in 0.1 minute, and 0% B for 10 minutes. Flow rate=1 mL/minute.

Detection of products was by UV absorption at 260 nm. Integration was performed by the internal program on the LC-500 FPLC Control panel. Relative rates for the alkyl amines and imidazoles are based upon the amount of remaining substrate, m7GpppG, measured against the internal standard, NAD, at t=0 hours and t=12 hours. Relative rates for the copper(II) complexes are based upon the amount of remaining substrate, m7GpppG, measured against the internal standard, NAD, and that of the control (buffer only) under the same reaction conditions. For UV analysis of the reactants and products, peaks were collected during the course of chromatography and then scanned separately using a photodiode array detector.

Example 3

Reaction rates and product analysis:

Of the compounds examined, the most reactive upon the 5' cap structure, m7GpppG, are the copper complexes. Cu(II)-ortho-phenanthroline hydrolyzes 52% of the starting material after 24 hours at 37° C. This metal complex yields as products GMP, m7GMP, GDP and m7GDP, as shown by chromatography. Product analysis was performed by coinjection experiments utilizing commercially available standards and by UV spectral analysis. These products indicate that hydrolysis of the phosphoanhydride linkage of the substrate is occurring. Further investigation of the reaction between Cu(II):orthophenanthroline and both the asymmetric and symmetric phosphoanhydrides, m7GpppG and GpppG, showed that the ratio of metal complex to the substrate must be greater than or equal to 2:1 in order to observe hydrolysis under the times (up to 7 days), temperatures (22° C., 37° C., 60° C.) and reactant conditions studied. Thus, it is presently believed that these reactions are not catalytic, since turnover was not observable.

In comparison to the metal complexes, the aromatic and alkyl amines were relatively unreactive. In order to observe these reactions within a reasonable time frame (24 hours), the temperature and concentrations were drastically increased over those used in the metal complex reactions. The relative reactivities of the amines with m7GpppG are shown in Table 1.

TABLE 1

| Reagent | Rel. reactivity upon m7GpppG |
| --- | --- |
| Triethylene tetramine | 1.0 |
| 1,5,9-Triazacyclododecane | 0.8 |
| Histamine | 0.24 |
| Diethylene triamine | 0.10 |
| Imidazole | 0.05 |
| N-methylimidazole | 0.05 |
| Pyridine | 0.01 |

Of the amines assessed (imidazole, N-methylimidazole, histamine, pyridine, 1,5,9-triazacyclododecane, diethylene triamine and triethylene tetramine), triethylene tetramine was most reactive, yielding a 47% loss of starting material after 6 hours at 60° C. The products obtained from reactions of the amines, both alkyl and aromatic, were different from those obtained with the metal complex reactions. Based on its level of reactivity and looking toward other antisense oligonucleotides equipped with such reactive moieties, a more extensive analysis was conducted using triethylene tetramine.

To further define and locate the site(s) of reaction of triethylene tetramine upon the 5' cap structure, three additional substrates were used: GpppG, GMP, and m7GMP.

This reaction set allowed differentiation between chemistry occurring at the phosphoanhydride linkages vs. chemistry occurring at either of the guanine bases. After 12 hours at 60° C., 500 mM triethylene tetramine, 1 mM substrate, no reaction is observed with either GpppG or GMP, whereas 68% loss of m7GMP is observed under these conditions, a loss comparable to that of the complete cap substrate. These results indicate that the primary or initiating reaction center for triethylene tetramine is located solely on the N7-methylated guanosine residue, not the phosphoanhydride linkage nor the unmethylated guanosine residue.

In general, the sites of reactivity for the metal complexes upon the 5' cap structure are different from those of the amines; the metal complexes that we have examined preferentially hydrolyze the triphosphoanhydride linkage, whereas the amines (exemplified by triethylene tetramine) preferentially react with the 7-methylguanosine residue. This is shown in Table 2:

TABLE 2

| (Sites of reactivity shown in bold:) | |
|---|---|
| Metal complexes: | Amines: |
| m7GpppG | m7GpppG |

Example 4

Chemical synthesis of oligonucleotides:

Unmodified oligonucleotides were synthesized on an automated DNA synthesizer (Applied Biosystems model 380B) using standard phosphoramidite chemistry with oxidation by iodine.

Example 5

Synthesis of 5' methylated guanosine (m7G)-capped oligoribonucleotides:

Capped oligoribonucleotides may be prepared by ligating commercially available m7GpppG to a chemically synthesized, 5' phosphorylated oligoribonucleotide, using T4 RNA ligase (Pharmacia). 2.5 mM m7GpppG, 0.3 mM oligoribonucleotide, 3.0 mM ATP, 30 units T4 RNA ligase were combined in 50 mM HEPES (pH 8.0) plus 10 mM $MgCl_2$, 0.7% DMSO. Reaction was for 48 hours at 4° C. Ligation yield was approximately 50%.

Example 6

Effect of 3' "dangling" nucleotides on the hybridization properties of an antisense oligodeoxyribonucleotide complementary to a 5'-capped oligoribonucleotide:

A 5'-capped oligonucleotide, 14 nucleotides in length exclusive of the cap, was synthesized by ligating commercially available m7GpppG (Pharmacia) to the chemically synthesized 5'-phosphorylated 14-mer, herein referred to as ISIS 2975 (see TABLE 3 below for sequence information), using T4 RNA ligase (Pharmacia). The desired product (50% ligation yield) was gel purified under native conditions and extracted into distilled water by crushing and soaking. Verification of capped product was done by comparison of the gel mobilities of the starting material (faster) and purified product (slower), and by the observation that the capped product (referred to herein as ISIS m7G2975) was insensitive to dephosphorylation with calf alkaline phosphatase (Boehringer Mannheim) while the 5'-phosphorylated starting material, ISIS 2975, was dephosphorylated under the same reaction conditions.

Two antisense oligonucleotides, ISIS 3043 and ISIS 3044, complementary to ISIS 2975 were synthesized. The sequences of these three oligonucleotides are shown in TABLE 3.

TABLE 3

| ISIS No. | Sequence (5'-3') | | | | | | Seq. ID No. |
|---|---|---|---|---|---|---|---|
| ISIS-2975 | CUA | UAA | GGA | UCA | CG | | 1 |
| ISIS-3044 | GTC | ATC | CTT | ATA | GC | | 2 |
| ISIS-3043 | GTC | ATC | CTT | ATA | GCG | C | 3 |

ISIS 3044, is a 14-mer complementary to ISIS 2975 base for base in the 14-base oligoribonucleotide region. ISIS 3043, a 16-mer, has two additional noncomplementary nucleotides, G and C, at its 3' end (which upon specific hybridization with the capped ISIS m7G2975 would be opposite the cap structure). Each antisense oligonucleotide was mixed 1:1 with ISIS m7G2975 at a concentration of 3 µM in 100 mM sodium and 10 mM phosphate (pH 7.0). Each sample was then heat denatured at 85° C. for 5 minutes and slowly cooled to room temperature. Thermal melts were then conducted over a temperature range from 10° C. to 90° C. using a Gilford Response II at steps of 0.5° C. The $T_m$s were determined by taking the first derivative of the melt profiles. The thermal melt profiles for the ISIS m7G2975:ISIS 3044 duplex and the ISIS m7G2975:ISIS 3043 duplex were compared. For the ISIS 3043:ISIS m7G2975 duplex, the $T_m$ was found to be 41.5° C.; for the ISIS 3044:ISIS m7G2975 duplex, the $T_m$ was found to be 42.5° C. These $T_m$s are identical within experimental error.

This result indicates that additional dangling nucleotides at the 3' end of an antisense oligonucleotide directed to the 5' terminus of a capped RNA will not alter the hybridization properties of the oligonucleotide as a result of interactions between these dangling nucleotides and the 5' cap structure of the transcript. These results indicate that attachment of a moiety which binds or reacts with the 5' cap of mRNA to the 3' end of an antisense molecule should be possible without perturbing the hybridization properties of the antisense molecule to the RNA.

Example 7

Enhancement of complexation (of eIF-4E) by "dangling" nucleotide composition:

(A) A 5'-capped 20-mer oligoribonucleotide, comparable to the 5' terminal sequence of the ICAM-1 cytokine-induced transcript, was utilized as the RNA substrate. The 5'-capped oligoribonucleotide was enzymatically synthesized by T7 RNA polymerase from a single-stranded DNA template, and its sequence is shown in Table 4, (B) antisense oligodeoxyribonucleotides were synthesized by standard phosphoramidite automated chemical procedures, and their sequences are shown in Table 4.

RNA substrate and each antisense oligonucleotide were individually mixed in buffer and heat-denatured at 90° C. for 1 minute. Samples were slowly cooled to room temperature over 15 minutes. 6 pM of eIF-4E was added and samples were stored at 0° C. for 10 minutes. Final incubation conditions: 1000 cpm $^{32}$P-labeled RNA substrate, 1.2 µM eIF-4E, 1 µM antisense oligonucleotide in 40 mM HEPES (pH 7.4) and 100 mM KCl. Samples were analyzed by polyacrylamide gel electrophoresis under non-denaturing conditions.

The results indicated that all the antisense oligonucleotides caused enhanced formation of the eIF- 4E:m7GpppRNA complex, with enhancements ranging from 110% to 220%.

TABLE 4

Sequences of RNA substrate and antisense oligonucleotides (A) RNA m7GpppGAGCUCCUCUGCUACUCAGA (B) Antisense oligonucleotides

TCTGAGTAGCAGAGGAGCTCA [SEQ. ID NO. 4]

TCTGAGTAGCAGAGGAGCTCT [SEQ. ID NO. 5]

TCTGAGTAGCAGAGGAGCTCC [SEQ. ID NO. 6]

Example 8

Tethering of triethylene tetramine to the 3' terminus of an oligonucleotide via a modified uridine tether:

50 µM ISIS 3251 (CTCTGAGTAGCAGAGGAGC, SEQ. ID NO. 7) was oxidized with 10 mM sodium periodate in the presence of 100 mM sodium acetate (pH 5.1) for 4 hours at 4° C. The reaction was quenched with glycerol and the oligonucleotide product was precipitated from solution with ethanol. The ethanol supernatent was discarded and the precipitate dried under vacuum. 100 µM Oxidized oligonucleotide product, 10 mM triethylene tetramine and 400 mM sodium bicarbonate (pH 9.2) were stirred at room temperature for 3 hours. Sodium cyanoborohydride (in excess of 10 equivalents) was added directly to the conjugation reaction solution and stirred at 4° C. for 1 hour. The conjugated product was purified by standard anion exchange chromatography utilizing a Pharmacia FPLC system.

Example 9

Inhibition of complexation of eIF-4E protein to the 5' cap structure of mRNA by antisense oligonucleotide having triethylene tetramine tethered to the 3' end:

It has been demonstrated that the 5' cap structure acts as a recognition element for proteins associated with the metabolism of messenger RNA. Eukaryotic initiation factor 4E (eIF-4E) is one such protein shown to play a role in the initiation of translation [Rhoads, R. E. *Trends Biochem. Sci.* 13 52–56 (1988); Sonenberg et al. *Proc. Natl. Acad. Sci. USA* 75 4843–4847 (1978)]. The availability of the 5' cap-specific protein, eIF-4E, allows a mechanism-based method of analysis to be utilized for the development of 5' cap-specific antisense oligonucleotide chemistry. Efficacy of the antisense oligonucleotides has been measured via a gel shift assay which separates the 5'-capped oligoribonucleotides which are complexed to the protein from those which are free in solution. Quantitation of the two RNA species has been performed utilizing $^{32}$P-labeled RNA and a Molecular Dynamics PhosphorImager. Results given below demonstrate that antisense oligonucleotides equipped with triethylene tetramine at the 3' terminus inhibit the complexation of eIF-4E to the 5'-capped oligoribonucleotide.

Experimental:

(A) a 23-nucleotide 5' capped oligoribonucleotide was utilized as the m7GpppRNA substrate. The 5'-capped oligoribonucleotide was synthesized by ligation of the enzymatically synthesized 5'-capped tetramer, m7GpppGAGC, to the chemically synthesized oligoribonucleotide 5'-pAGCUCCUCUGCUACUCAGA-FITC-3' (FITC is fluorescein 5-isothiocyanate), using T4 RNA ligase, (B) antisense oligonucleotides analyzed are (1) ISIS 3251 [SEQ.ID NO. 7], and (2) ISIS 3251T.

(A) RNA
5'                                                    3'
m7GpppGAGCAGCUCCUCUGCUACUCAGA-FITC (B) Antisense oligonucleotides
    5'                              3'
(1) CTCTGAGTAGCAGAGGAGCr[U]
(2) CTCTGAGTAGCAGAGGAGC[U]-Tren The oligonucleotides were mixed in buffer and heat-denatured at 90° C. for 1 minute. Samples were slow-cooled to room temperature over a period of 15 minutes. 1.6 pM of eIF-4E was added, samples were stored at 0° C. for 10 minutes, and then analyzed by gel electrophoresis. The Tren-equipped oligonucleotides exhibited a decrease in complexation of eIF-4E to capped mRNA when compared to the same oligonucleotide without tethered Tren. Thus, a reactive moiety, coupled via a tether to an oligonucleotide targeting portion, modulates the binding of translation factor eIF-4E to a particular 5'-capped RNA molecule.

Example 10

Cleavage of cap from 5'capped oligoribonucleotide by lanthanide complexes:

Radiolabeled 5'-capped oligoribonucleotides were enzymatically synthesized from a single stranded DNA template using T7 RNA polymerase with the addition of m7GpppG to the reaction mixture. Internally radiolabeled RNA was synthesized by the addition of [α-P32]-nucleotide triphosphates to the polymerase reaction, and 3' labeled RNA was synthesized by enzymatic ligation of $^{32}$pCp to the 3' end of unlabeled RNA using T4 RNA ligase. DNA complements were synthesized by standard phosphoramidite synthetic procedures. Lanthanide complexes have been described by Morrow, J. R. [(1994) *Adv. Inorg. Biochem.* 9:41–74] and McMurry et al. [(1989) *Science* 244:938–943]. EuCl$_3$ is commercially available (Aldrich). Radiolabeled 5'-capped RNA was prehybridized to complementary DNA in buffer by heat denaturation at 90° C. for 1 minute, cooled to room temperature (22° C., over 10 minutes), after which metal complexes were added. Final reaction concentrations were 1000 cpm radiolabeled RNA, 10 µM DNA complement, 20 mM HEPES (pH 7.1), 50 mM KCl and 100mM NaCl. Metal complex concentrations varied as shown in Table 5.

TABLE 5

5' cap cleavage of RNA by lanthanide and other metal complexes

| Set # | La complex  | Conc. (mM) | Rn. Cond. (°C./h) | Cleavage |
|-------|-------------|------------|-------------------|----------|
| 1     | Pr:DTPA-dien| 1          | 37/25             | No       |
| 1     | Eu:DTPA-dien| 1          | 37/25             | Yes      |
| 1     | Yb:DTPA-dien| 1          | 37/25             | No       |
| 1     | Co:Trien    | 1          | 37/25             | Yes      |
| 2     | EuCl$_3$    | 1          | 37/22             | Yes      |
| 2     | Eu:DTPA-dien| 1          | 37/22             | No       |
| 2     | Eu:THED     | 1          | 37/22             | Yes      |
| 3     | Eu:THP      | 0.1        | 37/4              | No       |
| 3     | La:TCMC     | 0.1        | 37/4              | No       |
| 3     | Eu:THED     | 0.1        | 37/4              | Yes      |
| 3     | Eu:DTPA-dien| 0.1        | 37/4              | No       |
| 4     | Eu:THED     | 0.01       | 37/4              | No       |
| 4     | Eu:THED     | 0.1        | 37/4              | Yes      |
| 4     | Eu:THED     | 1          | 37/4              | Yes      |

Example 11

Synthesis of Methyl-N-(S-benzoyl-2-mercaptoacetyl) glutamate (1):

2 mM Methyl-ε-(t-butyl)glutamate was dissolved in 25 mL of dichloromethane and reacted with 2.2 mM chloroacetylchloride. The reaction was quenched with 50% saturated sodium bicarbonate and the chloroacetyl intermediate was isolated. This intermediate was then dissolved in 5 mL of tetrahydrofuran and reacted with 2. mM thiobenzoic acid and 4 mM triethylamine. The resulting compound was isolated after work-up and redissolved in 10 mL of dichloromethane. Trifluoroacetic acid (0.5 mL) was added dropwise and the reaction mixture was stirred at room temperature for 16 hours. Upon final work-up, compound 1 was obtained as the product in an overall yield of 60%. It was characterized by thin-layer chromatography, mass spectroscopy and high resolution proton nmr in deuteriochloroform.

Example 12

Synthesis of oligonucleotide-ligand conjugate:

Compound 1 was activated for oligonucleotide chemistry as the N-hydroxysuccinimide ester by premixing 100 mM free acid of 1 with 200 mM N-hydroxysuccinimidesulfonate and 200 mM EDC for 25 minutes at room temperature. The ligand premix was added to 15 nM of the amine-modified oligonucleotide in 100mM sodium bicarbonate (pH 9.2). The oligonucleotide-MAG conjugate product was isolated on a NAP25 column (Pharmacia). Conjugated ligand was then deprotected by incubation of the oligonucleotide-MAG conjugate in 50 mM NaOH for 12 hours at 55° C. Sodium hydroxide was removed using a NAP25 column and the deprotected oligonucleotide-MAG conjugate was recovered as dried material by speedvac.

Example 13

Metallation of oligonucleotide-MAG conjugate:

1 μL of 1M NaOH was added to 5 μL of a 1 mM aqueous solution of the oligonucleotide-MAG conjugate. 1.5 μL of 10 mM $CuSO_4$ was then added to the solution. After stirring for 2 minutes at room temperature, 1 μL of 6M NaOH was added. After 5 minutes, 15 μL cold ethanol (−20° C.) was added which resulted in precipitation. The precipitated material was collected by microcentrifugation, washed with 80% cold ethanol and dried by speedvac.

Example 14

Cleavage analysis of oligonucleotide-metal complex conjugate:

3'-Radiolabeled 5'-capped RNA (A) was mixed with 10 μM oligonucleotide-MAG conjugate (B) in 10 mM HEPES (pH 7.4), 100 mM KCl and 10 mM NaCl. Reaction mixtures were incubated at 37° C. for 120 hours. Samples were analyzed by polyacrylamide gel electrophoresis under denaturing conditions. Cleavage of the 5' cap of RNA substrate, to the extent of 20%, was observed. The structure and sequence of oligonucleotide-MAG:Cu(II) conjugate (B) and its RNA substrate (A) are shown in FIG. 5.

Example 15

Synthesis of N-(2-mercaptopropionyl)glycine, MPG (2):

This compound was synthesized according to a procedure published by Sugiura et al. *J. Am. Chem. Soc.* 97 5577–5581 (1975).

Example 16

Figure 6:
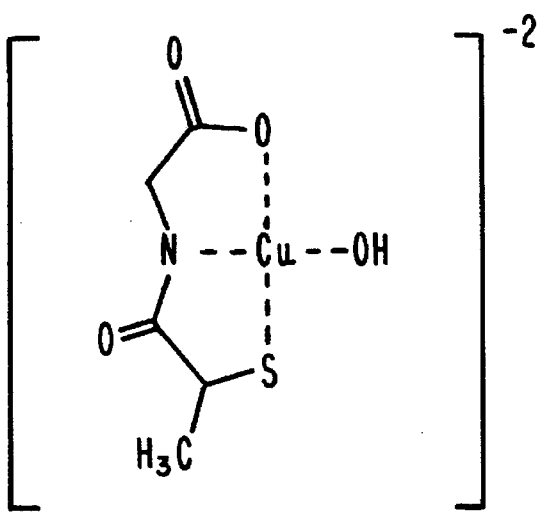
FIG. 6 depicts the structure of MPG:Cu(II) complex.

Cleavage analysis of MPG:Cu(II): The Cu(II) complex of N-(2-mercaptopropionyl)glycine was synthesized according to the method of Sugiura et al. *J. Am. Chem. Soc.* 97 5577–5581 (1975), and its structure is shown in FIG. 6. The 5'-capped target mRNA, hybridized to its DNA complement strand, was utilized as a substrate to test the cleavage activity of MPG:Cu(II) as a free reagent in solution. The target RNA was prehybridized with the DNA complement by heating the buffered solutions to 90° C. for 1 minute, followed by cooling to room temperature. After 10 minutes MPG:Cu(II) was added. An aliquot was removed for the zero time point and stored at −20° C. Solutions were buffered with 20 mM HEPES (pH 7.4), 50 mM KCl and 100 mM NaCl, and were incubated at 37° C. for 48 hours. Reaction samples were analyzed by polyacrylamide gel electrophoresis under denaturing condition. Cleavage of the 5' cap of RNA substrate was observed at MPG:Cu(II) concentrations of 0.15 mM (25% cleavage of the 5' cap) and 1.5 mM (56% cleavage of the 5' cap).

Example 17

Method for the removal of selected mRNAs from a pool of total cell mRNAs:

Total cell mRNA is isolated from cells by standard molecular biology procedures (Sambrook et al. (1989) *Molecular Cloning. A Laboratory Manual*, 2nd edition, Cold Spring Harbor Laboratory Press, Volume 2). The oligonucleotide-metal complex that is specifically hybridizable with specific mRNA is added to the isolated total cell mRNA in a buffered solution (HEPES, pH 7.4). After incubation under conditions determined to be sufficient for hybridization and cap cleavage to occur, the capped and uncapped mRNAs are separated with a 5' cap affinity column using the recombinant 5' cap-specific protein, eIF-4E. Alternatively, a 5' exonuclease, such as commercially available oligonucleotide-3'-nucleotidohydrolase derived from calf spleen (Boehringer Mannheim, Indianapolis, Ind.), is added to degrade uncapped transcripts. Degraded RNA products are removed by size exclusion chromatography or ethanol precipitation.

---

What is claimed is:

1. A composition for inhibiting the activity of an mRNA comprising:

a targeting portion which is an oligonucleotide or oligonucleotide analog specifically hybridizable with the 5' end of the mRNA;

a reactive portion which chemically modifies or cleaves the 5' cap structure of said mRNA, wherein said reactive portion is selected from the group consisting of an amine and a coordination complex of a metal; and a tether moiety connecting the targeting and reactive portions so that, upon hybridization of the targeting oligonucleotide or oligonucleotide analog to said mRNA, said reactive portion can contact the 5' cap of said mRNA.

2. The composition of claim 1 wherein said reactive portion comprises a coordination complex of a metal which cleaves the 5' cap structure.

3. The composition of claim 1 wherein said reactive portion comprises an amine.

4. The composition of claim 2 wherein said reactive portion comprises a coordination complex of a lanthamide metal.

5. The composition of claim 2 wherein said coordination complex comprises a metal ion selected from the group consisting of copper(II) and zinc(II).

6. The composition of claim 5 wherein said coordination complex of a metal is selected from the group consisting of zinc(II) complex of 1,10-ortho-phenanthroline, zinc(II) complex of bipyridine, copper(II) complex of 1,10-ortho-phenanthroline, copper(II) complex of bipyridine, copper(II) complex of N-(2-mercaptoacetyl)glutamate and copper(II) complex of N-(2-mercaptopropionyl)glycine.

7. The composition of claim 4 wherein the lanthanide metal complex is selected from the group consisting of Eu:DTPA-dien, EuCl$_3$ and Eu:THED.

8. The composition of claim 3 wherein said reactive portion comprises one or more alkyl amine moieties.

9. The composition of claim 8 wherein said alkyl amine moieties are selected from the group consisting of 1,5,9-triazacyclododecane, diethylene triamine and triethylene tetramine.

10. The composition of claim 3 wherein said reactive portion comprises one or more aromatic amine moieties.

11. The composition of claim 10 wherein said aromatic amine moieties are selected from the group consisting of imidazole, N-methylimidazole, histamine and pyridine.

12. The composition of claim 1 wherein said tether comprises from 1 to about 50 atoms.

13. The composition of claim 1 wherein said tether comprises from 1 to about 10 atoms.

14. The composition of claim 1 wherein said tether comprises at least one nucleotide.

15. The composition of claim 1 wherein said tether comprises at least one amino acid.

16. The composition of claim 12 where said tether has at least one side chain group.

17. The composition of claim 16 wherein said side chain is a cationic functional group.

18. The composition of claim 17 wherein said functional group is an amidine, an amine, a guanidinium residue, or a metal complex.

19. The composition of claim 16 wherein the side chain group is a heterocyclic base.

20. The composition of claim 19 wherein the base is a cytosine.

21. The composition of claim 1 wherein said targeting portion is an oligonucleotide or oligonucleotide analog comprising from about 5 to about 50 base units.

22. The composition of claim 21 wherein said targeting portion is an oligonucleotide or oligonucleotide analog comprising from about 8 to 25 base units.

23. The composition of claim 1 wherein said targeting portion is an oligonucleotide analog having at least one phosphodiester bond replaced with a sulfur-containing linkage.

24. The composition of claim 23 wherein said sulfur-containing linkage is a phosphorothioate moiety.

25. The composition of claim 1 wherein said targeting portion is an oligonucleotide or oligonucleotide analog which specifically hybridizes to immature pre-mRNA.

26. A composition for inhibiting the binding of eukaryotic initiation factor-4E to an RNA comprising:

a targeting portion which is an oligonucleotide or oligonucleotide analog specifically hybridazable with the 5' end of the mRNA;

a reactive portion which chemically modifies or cleaves the 5' cap structure of said mRNA, wherein said reactive portion is selected from the group consisting of an amine and a coordination complex of a metal; and a tether moiety connecting the targeting and reactive portions so that, upon hybridization of the targeting oligonucleotide or oligonucleotide analog to said mRNA, said reactive portion can contact the 5' cap of said mRNA.

27. A method of inhibiting the production of a protein by a eukaryotic cell comprising contacting the coll in vitro with a composition comprising:

a targeting portion which is an oligonucleotide or oligonucleotide analog specifically hybridizable with the 5' end of the mRNA encoding said protein;

a reactive portion which chemically modifies or cleaves the 5' cap structure of said mRNA, wherein said reactive portion is selected from the group consisting of an amine and a coordination complex of a metal; and a tether moiety connecting the targeting and reactive portions so that, upon hybridization of the targeting oligonucleotide or oligonucleotide analog to said mRNA, said reactive portion can contact the 5' cap of said mRNA.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
  ( A ) LENGTH: 14
  ( B ) TYPE: nucleic acid
  ( C ) STRANDEDNESS: single
  ( D ) TOPOLOGY: unknown ( x i ) SEQUENCE DESCRIPTION: SEQ ID NO: 1:

CUAUAAGGAU CACG                                                          14

( 2 ) INFORMATION FOR SEQ ID NO: 2:

( i ) SEQUENCE CHARACTERISTICS:
    ( A ) LENGTH: 14
    ( B ) TYPE: nucleic acid
    ( C ) STRANDEDNESS: single
    ( D ) TOPOLOGY: unknown ( x i ) SEQUENCE DESCRIPTION: SEQ ID NO: 2:

GTCATCCTTA TAGC                                                          14

( 2 ) INFORMATION FOR SEQ ID NO: 3:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: unknown ( x i ) SEQUENCE DESCRIPTION: SEQ ID NO: 3:

GTCATCCTTA TAGCGC                                                        16

( 2 ) INFORMATION FOR SEQ ID NO: 4:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: unknown ( x i ) SEQUENCE DESCRIPTION: SEQ ID NO: 4:

TCTGAGTAGC AGAGGAGCTC A                                                  21

( 2 ) INFORMATION FOR SEQ ID NO: 5:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: unknown ( x i ) SEQUENCE DESCRIPTION: SEQ ID NO: 5:

TCTGAGTAGC AGAGGAGCTC T                                                  21

( 2 ) INFORMATION FOR SEQ ID NO: 6:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: unknown ( x i ) SEQUENCE DESCRIPTION: SEQ ID NO: 6:

TCTGAGTAGC AGAGGAGCTC C                                                  21

( 2 ) INFORMATION FOR SEQ ID NO: 7:

( i ) SEQUENCE CHARACTERISTICS:
    ( A ) LENGTH: 19

-continued

```
( B ) TYPE: nucleic acid
( C ) STRANDEDNESS: single
( D ) TOPOLOGY: unknown ( x i ) SEQUENCE DESCRIPTION: SEQ ID NO: 7:

CTCTGAGTAG CAGAGGAGC                                              19
```